(12) United States Patent
Hirth

(10) Patent No.: US 8,491,504 B2
(45) Date of Patent: Jul. 23, 2013

(54) DEVICES AND METHODS FOR MONITORING SIT TO STAND TRANSFERS

(75) Inventor: Victor A. Hirth, Columbia, SC (US)

(73) Assignee: University of South Carolina, Columbia, SC (US)

( * ) Notice: Subject to any disclaimer, the term of this patent is extended or adjusted under 35 U.S.C. 154(b) by 125 days.

(21) Appl. No.: 12/850,151

(22) Filed: Aug. 4, 2010

(65) Prior Publication Data

US 2011/0105956 A1 May 5, 2011

Related U.S. Application Data

(60) Provisional application No. 61/231,106, filed on Aug. 4, 2009.

(51) Int. Cl.
*A61B 5/11* (2006.01)

(52) U.S. Cl.
USPC .................. 600/595; 600/587; 297/217.4

(58) Field of Classification Search
USPC .................. 600/587, 595; 297/217.4
See application file for complete search history.

(56) References Cited

U.S. PATENT DOCUMENTS

| | | | | |
|---|---|---|---|---|
| 6,669,286 B2 * | 12/2003 | Iusim | | 297/217.4 |
| 7,141,026 B2 * | 11/2006 | Aminian et al. | | 600/595 |
| 7,985,193 B2 * | 7/2011 | Thorsteinsson et al. | | 602/16 |
| 8,079,277 B2 * | 12/2011 | Bang et al. | | 73/865.4 |
| 8,092,355 B2 * | 1/2012 | Mortimer et al. | | 482/142 |
| 8,115,641 B1 * | 2/2012 | Dempsey | | 340/573.1 |
| 8,206,325 B1 * | 6/2012 | Najafi et al. | | 600/595 |
| 8,231,555 B2 * | 7/2012 | Skelton et al. | | 600/595 |
| 8,301,575 B2 * | 10/2012 | Bonnet et al. | | 706/12 |
| 2002/0171272 A1 * | 11/2002 | Iusim | | 297/217.4 |
| 2004/0015103 A1 * | 1/2004 | Aminian et al. | | 600/595 |
| 2004/0130452 A1 * | 7/2004 | Cherubini | | 340/573.7 |
| 2005/0054381 A1 * | 3/2005 | Lee et al. | | 455/557 |
| 2005/0278409 A1 * | 12/2005 | Kutzik et al. | | 709/200 |
| 2006/0149338 A1 * | 7/2006 | Flaherty et al. | | 607/49 |
| 2006/0149905 A1 * | 7/2006 | Park et al. | | 711/141 |
| 2006/0217986 A1 * | 9/2006 | Mizuki et al. | | 704/275 |
| 2007/0027369 A1 * | 2/2007 | Pagnacco et al. | | 600/301 |
| 2007/0112274 A1 * | 5/2007 | Heitzmann et al. | | 600/485 |
| 2009/0012921 A1 * | 1/2009 | Bonnet et al. | | 706/12 |
| 2009/0030345 A1 * | 1/2009 | Bonnet et al. | | 600/587 |
| 2009/0062092 A1 * | 3/2009 | Mortimer et al. | | 482/142 |
| 2009/0082699 A1 * | 3/2009 | Bang et al. | | 600/595 |
| 2009/0234262 A1 * | 9/2009 | Reid et al. | | 601/152 |
| 2009/0254003 A1 * | 10/2009 | Buckman | | 600/595 |
| 2010/0010390 A1 * | 1/2010 | Skelton et al. | | 600/595 |
| 2010/0036289 A1 * | 2/2010 | White et al. | | 600/595 |
| 2010/0096445 A1 * | 4/2010 | Lu et al. | | 235/375 |
| 2011/0018682 A1 * | 1/2011 | Weisfeld | | 340/5.7 |
| 2011/0288379 A1 * | 11/2011 | Wu | | 600/301 |
| 2012/0025966 A1 * | 2/2012 | Nakanishi et al. | | 340/436 |
| 2012/0059284 A1 * | 3/2012 | Eschler et al. | | 600/595 |
| 2012/0101411 A1 * | 4/2012 | Hausdorff et al. | | 600/595 |
| 2012/0130286 A1 * | 5/2012 | Miesel et al. | | 600/595 |

* cited by examiner

*Primary Examiner* — Sean Dougherty
(74) *Attorney, Agent, or Firm* — Dority & Manning, P.A.

(57) ABSTRACT

In certain embodiments of the present disclosure, a device for monitoring sit to stand transfers is provided. The device includes an electromechanical sensor and a computer, wherein the electromechanical sensor is configured to signal sit to stand transfers to the computer and the computer is configured to determine if the sit to stand transfers deviate from a normal sit to stand transfer pattern.

19 Claims, 2 Drawing Sheets

DEVICES AND METHODS FOR MONITORING SIT TO STAND TRANSFERS

CROSS-REFERENCE TO RELATED APPLICATION

The present application is based on and claims priority to U.S. Provisional Application 61/231,106 having a filing date of Aug. 4, 2009, which is incorporated by reference herein.

BACKGROUND

Health care needs and costs are estimated to rise in parallel with the rapidly growing geriatric population. When older adults become dependent or disabled, the burden for family and health care providers escalates. Being able to predict approaching disability for older adults could allow for intervention and prevention, which could in turn reduce such burdens as well as the associated costs.

As such, a need exists for a device that can assist in predicting approaching disability. Methods of utilizing such a device would also be of great benefit.

SUMMARY

In certain embodiments of the present disclosure, a device for monitoring sit to stand transfers is provided. The device includes an electromechanical sensor and a computer, wherein the electromechanical sensor is configured to signal sit to stand transfers to the computer and the computer is configured to determine if the sit to stand transfers deviate from a normal sit to stand transfer pattern.

In another embodiment of the present disclosure, a method for monitoring sit to stand transfers is provided. The method includes utilizing a device to signal a sit to stand transfer.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figure in which.

DETAILED DESCRIPTION OF INVENTION

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

The present disclosure is generally directed to a device for monitoring sit to stand transfers. The capacity to stand up from a seating surface is an indicator of physical motor capabilities for older adults. In accordance with the present disclosure, it has been determined that monitoring changes in sit to stand transfer can predict loss of function. The devices and methods of the present disclosure can be utilized to collect data and analyze such data to reveal approaching disability.

Figure 1:
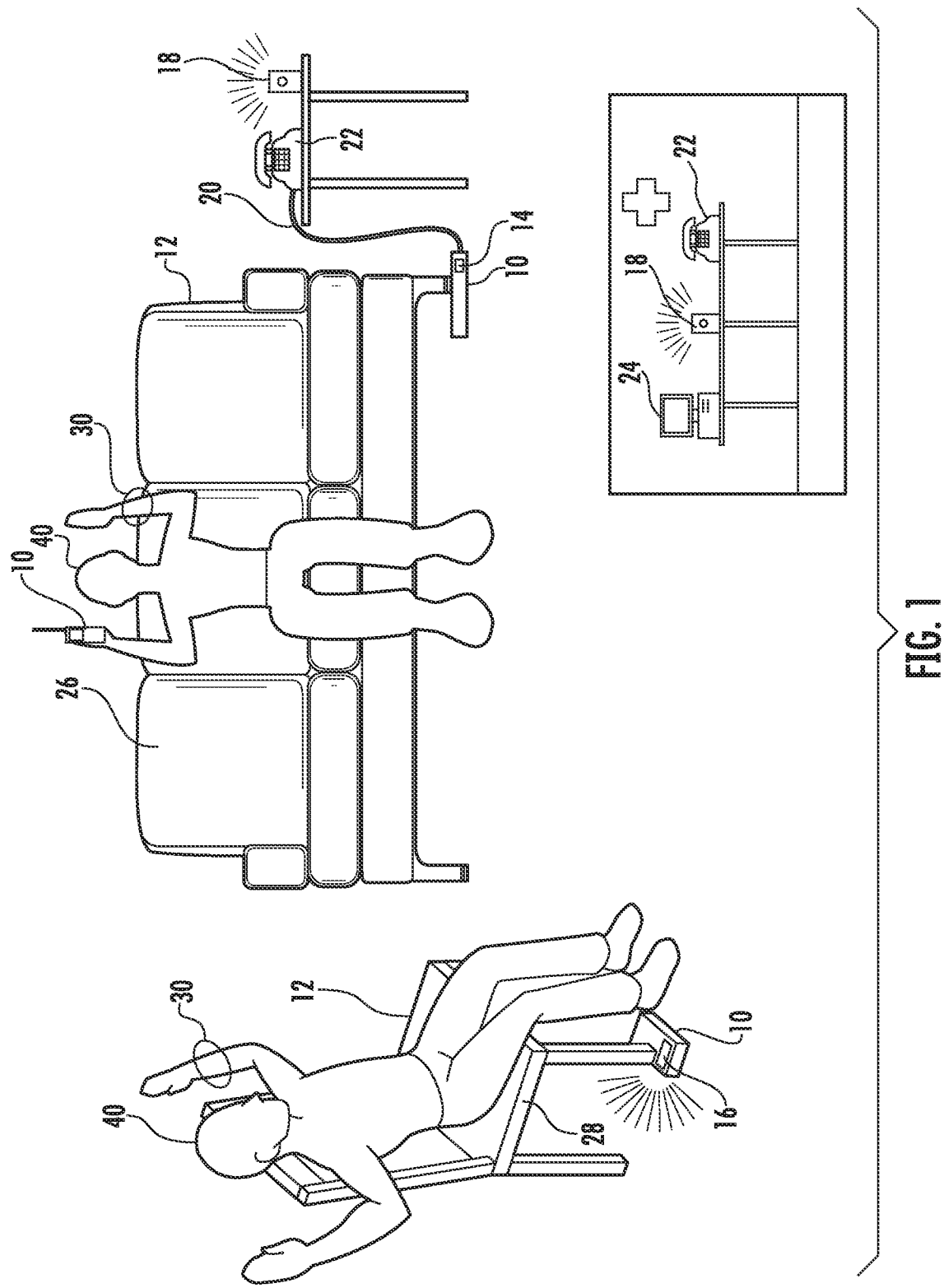
FIG. 1 illustrates the device in accordance with certain embodiments of the present disclosure.

In this regard, FIG. 1 illustrates one embodiment of a device 10 in accordance with the present disclosure. The device 10 is designed to be positioned on or under a seating surface 12. For instance, the device can be placed under the bottom of a leg of a chair or in the seat of a chair, or in any other suitable location on or around a chair so that the device 10 can register a sit to stand transfer. More than one device can be used concurrently and can function as a single device as will be described in more detail hereinafter. The technology is adaptable, and can be designed to easily fit any seating surface in any environment so that data is collected unobtrusively.

The device includes an electromechanical sensor that is configured to detect a sit to stand transfer. Any suitable electromechanical sensor can be utilized in accordance with the present disclosure. For instance, a film capable of producing an electromechanical response can be utilized.

Such a film can stretch in two perpendicular directions, and has a thickness of about 1 to about 200 μm, more particularly from about 50 to about 100 μm, still more particularly from about 65 to about 70 μm. The film can be comprised of thin layers of polyolefin with flat voids therebetween. The voids can be made of small compounded particles which form cavities that are closed when both axes are stretched. The thickness and elasticity of the film can be more than doubled when the air voids inside are injected with high pressure gas technology. The sensor can create a charge, corresponding to a change of thickness of the film, and this charge is relayed to software in a computer. Suitable electromechanical films are available from Emfit, Ltd. in Finland. Such films can achieve a strong electromechanical response.

The films can be based on a polyolefin material manufactured in a continuous biaxial orientation process that stretches the film in two perpendicular directions (machine direction and the transverse direction). Further the films can be expanded in thickness at high-pressure gas-diffusion-expansion (GDE) process.

The structure of such films can consist of flat voids separated by thin polyolefin layers. The films can have a thickness ranging from about 70 μm to about 80 μm. Voids can be made by compounding small particles, which function as rupture nuclei and forming closed lens like cavities in the film during the biaxial orientation. The voids can be enlarged by the GDE process.

A permanent electric charge can be injected into the material by corona charging it in high electric field. This causes electric breakdowns to occur inside the material, thus charging the void interfaces inside the film in order to form a material capable of interacting with its environment. Thin metal electrodes can, by way of example, be arranged by screen-printing them to polyester film and laminating them together with electromechanical film. Vacuum evaporation to both surfaces of the film is also possible for actuator purposes. Another way to arrange electrodes is using aluminum-polyester laminate and etching the electrode pattern prior laminating with electromechanical film Other suitable electromechanical sensors are also contemplated for use with the present disclosure. For example, load cells, accelerometers, or the like are suitable electromechanical sensors. However, one of ordinary skill in the art will appreciate that there are a number of other suitable electromechanical sensors that can be utilized. It should also be appreciated that more than one type of electromechanical sensor can be utilized in connection with a device of the present disclosure.

In addition to an electromechanical sensor, the device of the present disclosure also includes a computer. Any suitable computer can be utilized. The computer and the electromechanical sensor can be contained within a single housing or can be separate from one another in which case they can communicate either wirelessly or by wired connection. The devices and methods discussed herein can be implemented using servers, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, databases and applications can be implemented on a single system or distributed across multiple systems. Distributed components can operate sequentially or in parallel.

When data is obtained or accessed between a first and second computer system or component thereof, the actual data can travel between the systems directly or indirectly. For example, if a first computer accesses a file or data from a second computer, the access can involve one or more intermediary computers, proxies, and the like. The actual file or data can move between the computers, or one computer can provide a pointer or metafile that the second computer uses to access the actual data from a computer other than the first computer, for instance.

The various computer systems that can be utilized with the present disclosure are not limited to any particular hardware architecture or configuration. Embodiments of the methods and devices set forth herein can be implemented by one or more general-purpose or customized computing devices adapted in any suitable manner to provide desired functionality. The device(s) can be adapted to provide additional functionality complementary or unrelated to the present subject matter, as well. For instance, one or more computing devices can be adapted to provide desired functionality by accessing software instructions rendered in a computer-readable form. When software is used, any suitable programming, scripting, or other type of language or combinations of languages can be used to implement the teachings contained herein. However, software need not be used exclusively, or at all. For example, some embodiments of the methods and systems set forth herein can also be implemented by hard-wired logic or other circuitry, including, but not limited to application-specific circuits. Of course, combinations of computer-executed software and hard-wired logic or other circuitry can be suitable, as well.

Embodiments of the methods disclosed herein can be executed by one or more suitable computing devices. Such system(s) can comprise one or more computing devices adapted to perform one or more embodiments of the methods disclosed herein. As noted above, such devices can access one or more computer-readable media that embody computer-readable instructions which, when executed by at least one computer, cause the at least one computer to implement one or more embodiments of the methods of the present subject matter. Additionally or alternatively, the computing device(s) can comprise circuitry that renders the device(s) operative to implement one or more of the methods of the present subject matter.

Any suitable computer-readable medium or media can be used to implement or practice the presently-disclosed subject matter, including, but not limited to, diskettes, drives, and other magnetic-based storage media, optical storage media, including disks (including CD-ROMS, DVD-ROMS, and variants thereof), flash, RAM, ROM, and other memory devices, and the like.

The present disclosure also can also utilize a relay of communicated data over one or more communications networks. It should be appreciated that network communications can comprise sending and/or receiving information over one or more networks of various forms. For example, a network can comprise a dial-in network, a local area network (LAN), wide area network (WAN), public switched telephone network (PSTN), the Internet, intranet or other type(s) of networks. A network can comprise any number and/or combination of hard-wired, wireless, or other communication links.

The computer of the present disclosure includes software that can record data from an electromechanical sensor as described herein and determine a normal baseline of sit to stand transfers as well as a deviation from such a baseline. In this regard, in certain embodiments, the device of the present disclosure is configured to have a training mode in which baseline data is obtained on the sit to stand transfers for a user. The length of the training period should be sufficient to provide baseline sit to stand transfer pattern data. The length of the training period may be as short as seven days or as long as one month or longer. Sit to stand transfer patterns can be determined by the number of sit to stand transfers, the location of the sit to stand transfer (if more than one location is being monitored), and the duration between sit to stand transfers. These factors, as well as the day of the week (weekend versus weekday, for example) can lead to multiple sit to stand transfer patterns for a user.

In addition, the software can include a pre-programmed baseline that is based on predetermined sit to stand patterns. Such a pre-programmed baseline can be stored in the computer according to age, sex, weight, or the like to most closely match the predicted sit to stand characteristics of a user. The user can select from such variables that correspond to their characteristics.

Figure 2:
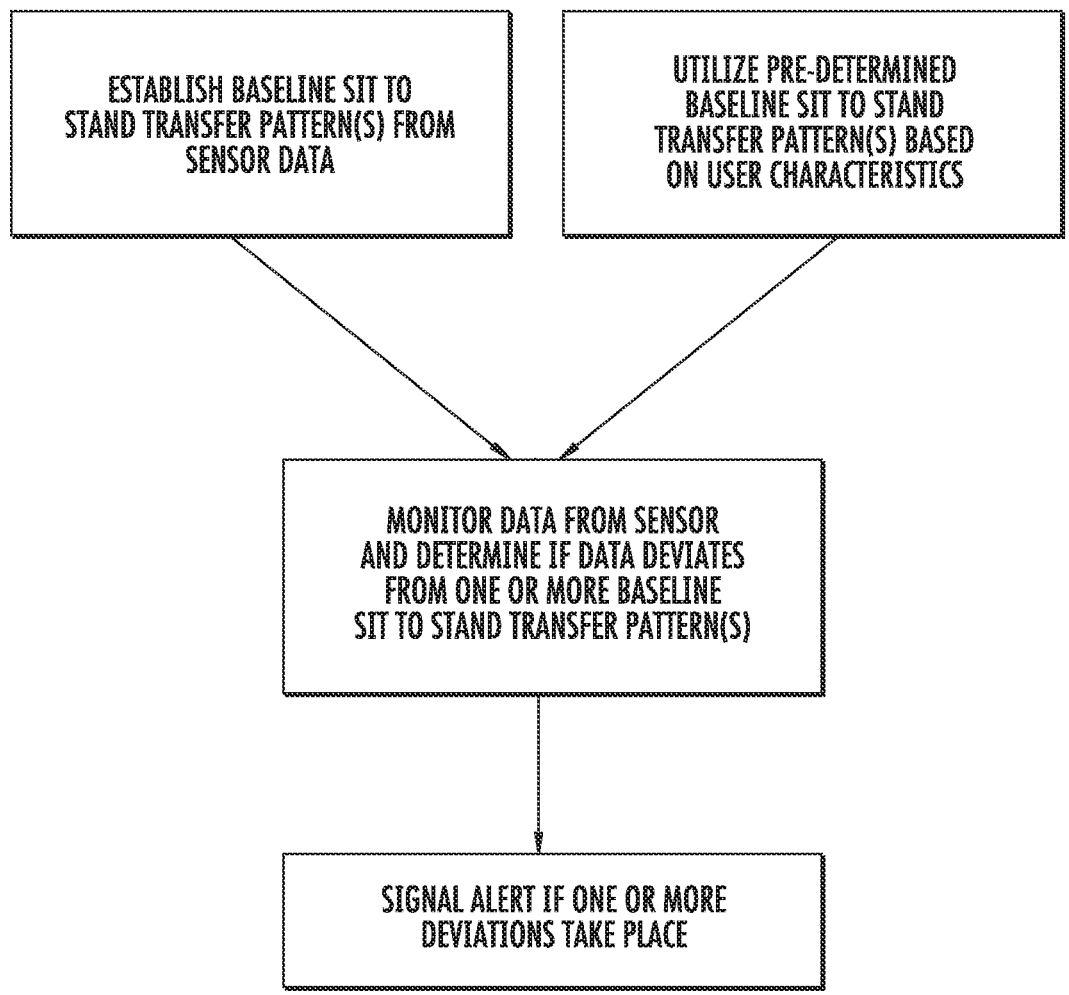
FIG. 2 illustrates a method for monitoring sit to stand transfers in accordance with certain embodiments of the present disclosure.

The software can monitor data from the electromechanical sensor and determine if the data deviates from one or more of the baseline patterns. FIG. 2 illustrates a method for monitoring sit to stand transfers in accordance with certain embodiments of the present disclosure. In the event of a deviation, the software can either wait for further deviations, or signal an alert immediately. The alert can be audible, visual, and/or can be transmitted, either to another part of the device or to another device altogether.

For example, in accordance with certain embodiments of the present disclosure, the computer can calculate an average number of sit to stand transfers per day by calculating the number of sit to stand transfers over x number of days and dividing that number by x. Similarly, an average can be taken for the number of sit to stand transfers during a certain time of day or any other desired period of time. Once one or more sit to stand transfer pattern averages for a pre-determined period of time are calculated, the software can signal a deviation based upon at least about a 10% decrease in the average number of sit to stand transfers for a subsequent monitored period of time. In certain embodiments, the software can signal a deviation based upon at least about a 5% decrease in the average number of sit to stand transfers for a certain period. In still other embodiments, the software can signal a deviation based upon at least about a 1% decrease in the average number of sit to stand transfers for a certain period. Again, as described above, in the event of a deviation the software can either wait for further deviations, or signal an alert immediately.

Turning again to FIG. 1, the device 10 can include a speaker 14, light 16, or other mechanism, such as a display, to provide notification of an alert. In addition, the device 10 can transmit an alert through a wired connection (such as a phone line 20 or data line), wirelessly, or some combination of both. For instance, the device 10 can include a wireless transmitter and can transmit the alert to an alert station 18. The wireless communication can use any of a plurality of communications standards, protocols and technologies, including but not limited to Global System for Mobile Communications (GSM), Enhanced Data GSM Environment (EDGE), wideb and code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS)), Radio-frequency identification (RFID) or any other suitable communication protocol, or any combination thereof, including communication protocols not yet developed as of the filing date of this document. Alert station 18 can provide notification of the alert as described above. Alert station 18 can be installed in a plurality of locations to maximize the chance that the intended party or parties is/are notified when the alert occurs.

In addition to transmitting an alert to alert station 18, the alert can be transmitted to any other suitable device such as a telephone 22 (cell phone or landline), computer 24, or the like. For instance, the alert can be transmitted as a text message (such as an SMS) to a cell phone or as an email to a computer or to any other device that is compatible with the above-described communications standards, protocols and technologies.

As discussed previously, either a single device can be utilized to monitor deviations in sit to stand transfers or a plurality of devices can be utilized, acting as one device. Sit to stand transfer patterns can be determined by the number of sit to stand transfers by location of the sit to stand transfer if more than one location is being monitored. In such embodiments, an alert can be triggered if data from one of the electromechanical sensors in each device indicates a deviation from one or more of the baseline patterns. For instance, as illustrated in FIG. 1, the device 10 is located underneath sofa 26 and chair 28. The device 10 can trigger an alert if a deviation occurs from one or more of the baseline patterns established for each seating surface.

Further, in certain embodiments of the present disclosure, the devices can be utilized by more than one user 40 at the same time. For instance, each user can wear an identification item 30 such as a bracelet or the like that can emit a signal that can be detected by the device 10. For instance, any of the plurality of communications standards, protocols and technologies described herein can be utilized so that the device 10 can track which user or user(s) are present on a seating surface. In this manner, device 10 can trigger an alert if a deviation occurs from one or more of the baseline patterns established for each user.

In certain embodiments of the present disclosure, device 10 does not have to be positioned on or around a seating surface but can instead be designed to be positioned on a user. In this regard, any device suitable to detect a sit to stand transfer can be utilized. For instance, a handheld computer (such as an iPod, iPod Touch, or the like), a mobile phone, smart phone, or PDA (such as a Blackberry device, and/or an iPhone), or any other suitable handheld device that is capable of detecting a sit to stand transfer can be utilized.

By monitoring sit to stand transfers, deviations from the normal individual pattern will provide information on underlying patterns that will lead to disability. Recognizing the difference in an individual sit to stand pattern, the health care provider will be able to intervene earlier than is currently possible to provide an intervention, review medication, or check health status to prevent or delay approaching disability, which can lead to health complications or a fall.

When placed in the home, this technology can allow older adults to live independently longer than is currently possible because it provides a method of monitoring sit to stand transfers which are indicative of health parameters. For waiting rooms, physician offices, diagnostic centers, other health care facilities, or the like, the technology may provide information that can help determine the mobility and balance level of the patient. It will provide ambient technology that can also be used to prevent and/or predict falls. By keeping older adults healthy and active, they will maintain function and mobility, indirectly reducing dependence on caregivers and the health care system.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure so further described in such appended claims.

What is claimed:

1. A device for monitoring sit to stand transfers comprising:
   an electromechanical sensor and a computer,
   wherein the electromechanical sensor is configured to signal a number of sit to stand transfers to the computer and the computer is configured to determine if the number of sit to stand transfers deviate from a normal sit to stand transfer pattern and wherein the computer is configured to produce an alert if the number of sit to stand transfers deviate from a normal sit to stand transfer pattern.

2. The device of claim 1, wherein the electromechanical sensor comprises a film.

3. The device of claim 2, wherein the film comprises a polyolefin.

4. The device of claim 1, wherein the electromechanical sensor comprises a load cell.

5. The device of claim 1, wherein the alert is configured to be transmitted wirelessly.

6. The device of claim 1, further comprising an alert station, the alert station configured to receive the alert from the computer.

7. The device of claim 1, wherein the alert is configured to be transmitted via the internet.

8. The device of claim 1, wherein the device is configured to be positioned at a base of a seating surface so that the electromechanical sensor can signal sit to stand transfers.

9. The device of claim 1, wherein the device further comprises an RFID tag, the RFID tag configured to be placed on a user, the computer being capable of associating the sit to stand transfers with the user based upon the RFID tag.

10. The device of claim 1, wherein the device further comprises a plurality of RFID tags, the RFID tags configured to be placed on different users, the computer being capable of associating the sit to stand transfers with each different user based upon the RFID tag.

11. The device of claim 1, wherein the device is capable of signaling sit to stand transfers from a plurality of different seating surfaces.

12. The device of claim 1, wherein the electromechanical sensor and computer are not connected to one another by wire.

13. The device of claim 1 wherein the electromechanical sensor and computer are connected to one another by wire.

14. A method for monitoring sit to stand transfers comprising:
utilizing a device to signal a sit to stand transfer, the device comprising an electromechanical sensor and a computer, the electromechanical sensor signaling a number of sit to stand transfers to the computer and the computer determining if the number of sit to stand transfers deviate from a normal sit to stand transfer pattern, the computer producing an alert when the number of sit to stand transfers deviate from a normal sit to stand transfer pattern.

15. The method of claim 14, wherein the electromechanical sensor comprises a film.

16. The method of claim 14, further comprising seeking medical attention for the user in response to a deviation from a normal sit to stand transfer pattern.

17. The method of claim 14, wherein the electromechanical sensor comprises a load cell.

18. The method of claim 14, wherein the computer produces an alert if the sit to stand transfers deviate from a normal sit to stand transfer pattern.

19. The method of claim 14, wherein the device is positioned at a base of a seating surface so that the electromechanical sensor can signal sit to stand transfers.

* * * * *